United States Patent [19]

Beaupied

[11] Patent Number: 5,135,520
[45] Date of Patent: Aug. 4, 1992

[54] GARMENTS FOR CONCEALING AND SUPPORTING AN OSTOMY APPLIANCE

[76] Inventor: Dolores Y. Beaupied, 200 Inwood Dr., Ste. 106, Wheeling, Ill. 60090

[21] Appl. No.: 604,564

[22] Filed: Oct. 26, 1990

[30] Foreign Application Priority Data

Oct. 24, 1990 [CA] Canada .................................. 2028456

[51] Int. Cl.⁵ .............................................. A61F 5/44
[52] U.S. Cl. .................................................... 604/345
[58] Field of Search ................... 2/400, 401, 406, 405; 450/150, 155; 604/332–345

*Primary Examiner*—Randall L. Green
*Assistant Examiner*—R. Clarke
*Attorney, Agent, or Firm*—Wallenstein, Wagner & Hattis, Ltd.

[57] ABSTRACT

A variable closure device is provided for an ostomy garment having a pair of crisscross pocket forming panels configured to lie behind an ostomy device. The crisscross overlapping arrangement of the pocket forming panels forms an elongated slot above the crossover region. Panels are releasably joined together at their top portions over a range of relative positions, including spaced apart and overlapping conditions, so as to provide a measure of adjustment to the tension provided in support of the device, and to provide an improved degree of surrounding of the ostomy device flange when the ostomy device is emplaced relatively low on the user's abdomen. The variable closure device may be used with brief-type undergarments having a front and rear garment panels joined to the pocket forming panels to jockey style briefs having an insert panel attachable at the top to the waistband and at the bottom to the lower edges of the pocket forming panels. An open back version of the first type of garment is provided for bedtime wear and has supplemental leg bands attached thereto.

20 Claims, 5 Drawing Sheets

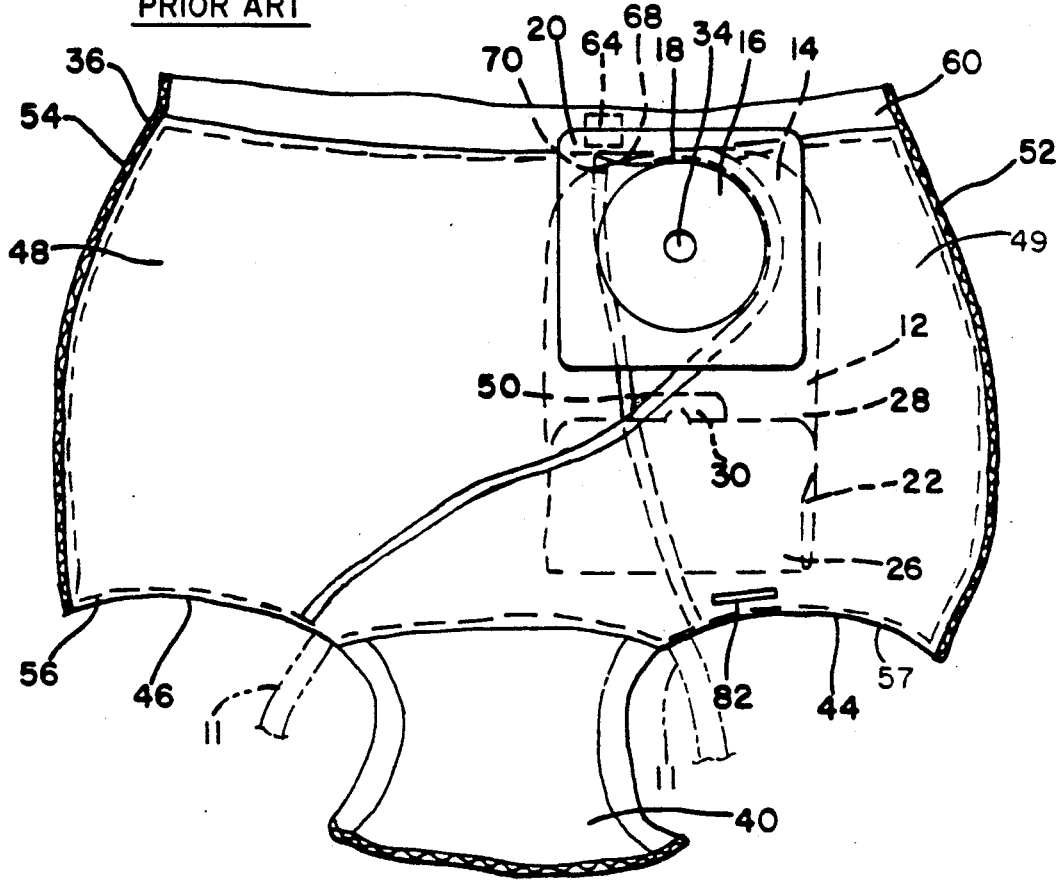
FIG_3_
PRIOR ART
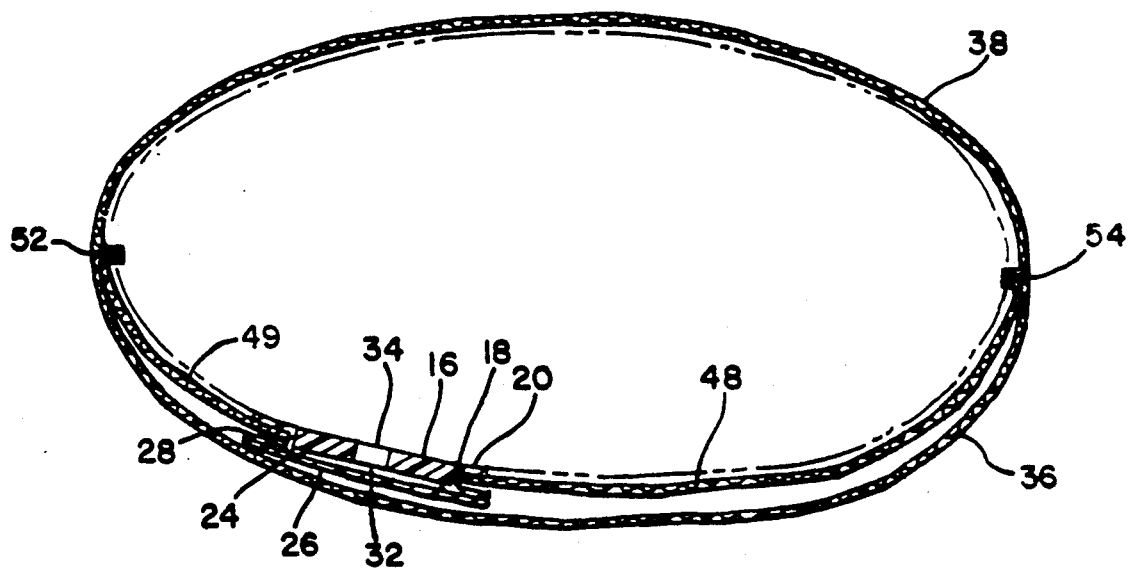
FIG_4_
PRIOR ART

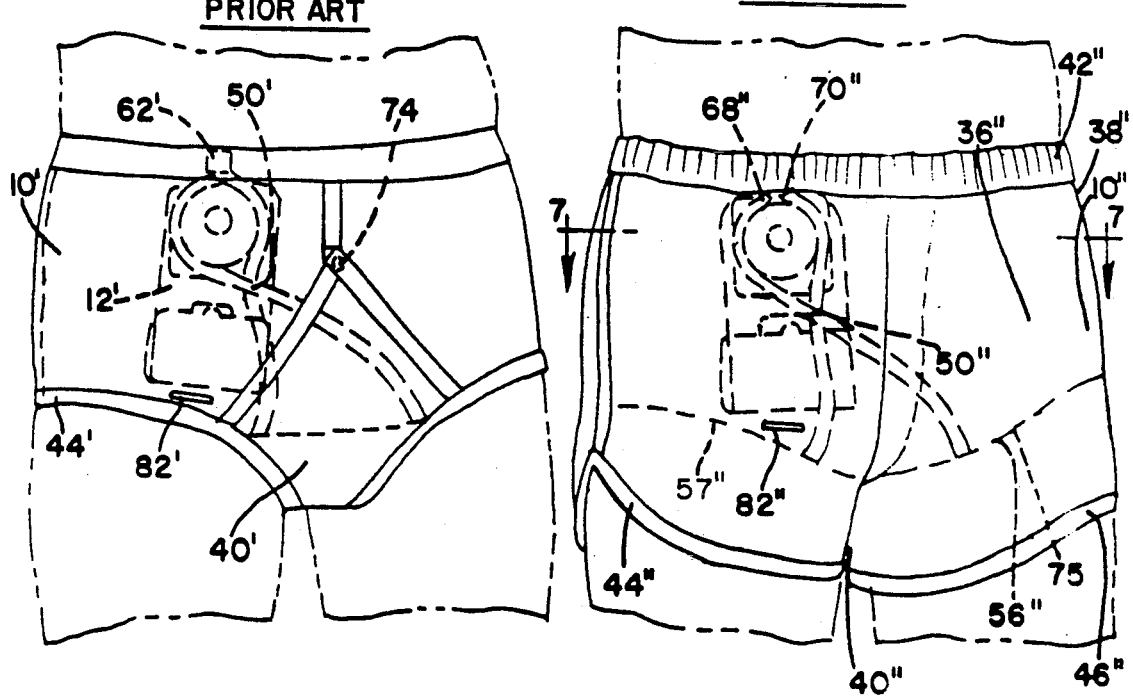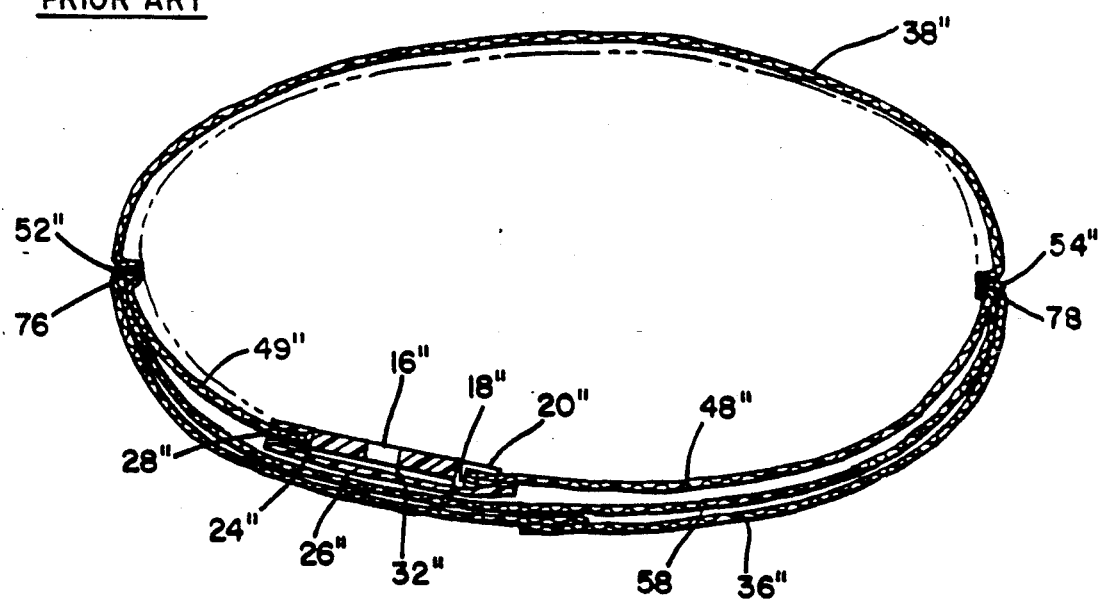

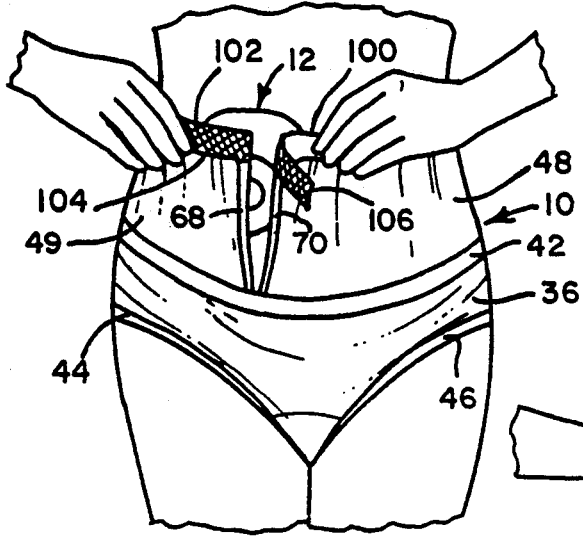
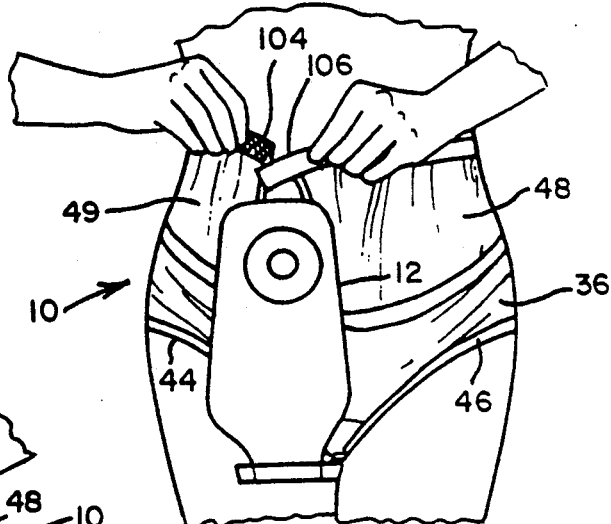
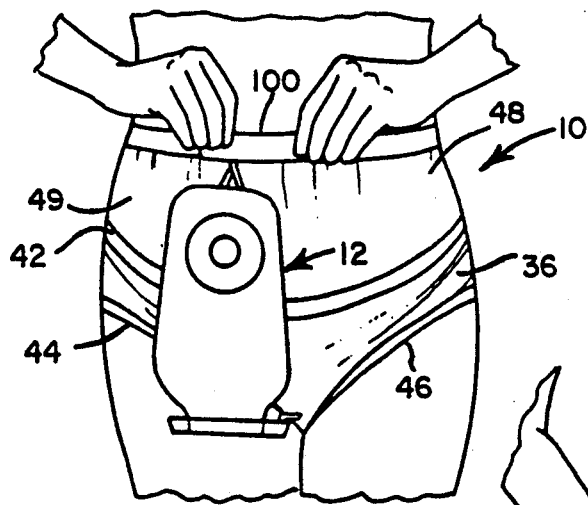
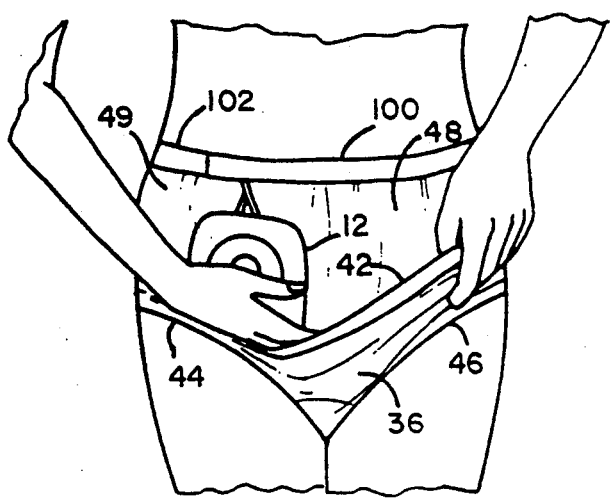

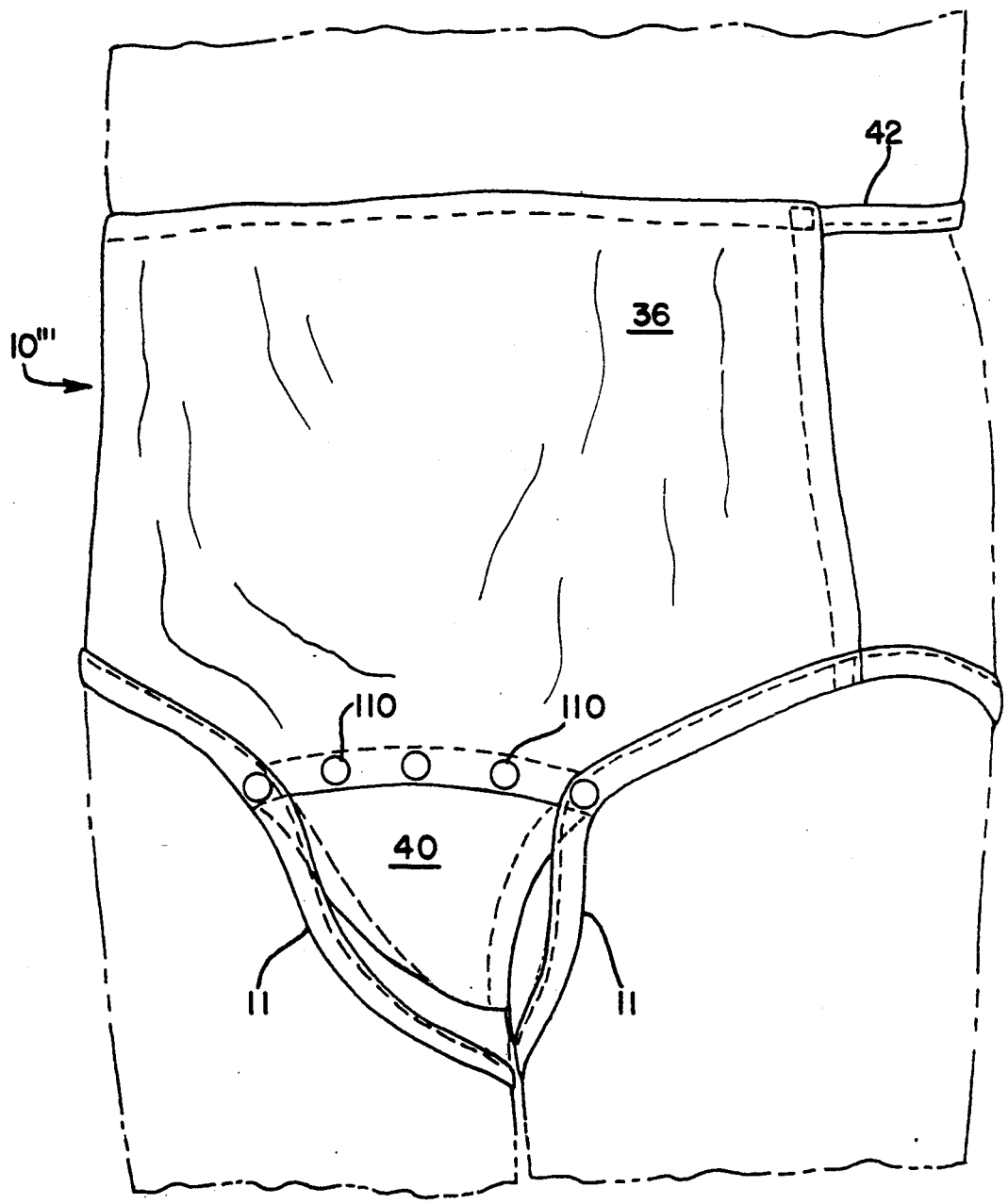
FIG_12

GARMENTS FOR CONCEALING AND SUPPORTING AN OSTOMY APPLIANCE

TECHNICAL FIELD

The present invention generally relates to ostomy garments worn by individuals required to use an ostomy appliance.

BACKGROUND OF THE INVENTION

U.S. Pat. No. 4,888,006 discloses an undergarment for use in conjunction with an ostomy appliance having upper and lower pouch portions and a flange member mounted to the upper pouch portion. The garment includes front, back and crotch garment panels interconnected together to form the outer portion of the garment. A retaining pocket is interposed between the front and back garment panels for receiving an ostomy appliance and is connected to the front garment panel. The retaining pocket includes a pair of pocket panels having lower edge portions configured for crisscross overlapping confrontation for confining the lower portion of the appliance above the region of overlap and upper edge portions configured to be drawn around opposite portions of the flange. The edge portions thus form a barrier between the appliance pouch and the user, and are movable with respect to each other below the overlap so that the upper terminus of the overlap defines the lower end of an adjustable slot for accommodating a range of positions of the flange. The upper edge portions of the pocket panels are permanently joined together to define the upper end of the slot. In one version of the appliance the lower edges of the pocket panels are secured to lower portions of the front garment panel to form the complete pocket. In another version an insert panel is interposed between the pocket panels and the front panel, and is secured at its top to the garment waistband. The pocket is completed by securing the lower edges of the pocket panels to the lower edge of the insert panel.

The ostomy garment is adaptable to various appliances and can accommodate appliances emplaced over a substantial range of positions on the abdomen. It would be desirable, however, to adapt the prior art garment to accommodate an even larger range of flange positions, while still providing secure retention and adequate closure around the flange.

SUMMARY OF THE INVENTION

Ostomy garments or the type described in the Background of Invention are adapted to provide an adjustable degree of support and closure around the flange of the ostomy device over a range of positions of placement of the device. This is accomplished by securing the upper edges of the pocket panels together at the upper end of the slot by releasable fastening means engagable over a range of positions. This is preferably accomplished by affixing a pair of self-adhering fabric tapes of the type manufactured under the trade name Velcro to the top edges of the pocket panels at the upper adjacent corners thereof. Once the slit-forming edges of the pocket panels have been stretched around the lower face of the flange member, the panel corners are secured to each other simply by pressing the corners together. The upper portion of the slit-defining edges of the pocket panels may be spaced at a distance from each other, or may be brought into a overlapping engagement, according to the desired tension, and according to the location of the flange on the user's abdomen. Relatively moderate degree of closure thus accommodates high flange placement, and overlapping end closure provides an improved upper surrounding capability for flanges emplaced lower down.

The foregoing improvement can be carried out in either of the previously mentioned versions of the garment, and in addition to a third form of garment having an open back and providing a cooler and less confining garment for sleeping.

Other advantages and aspects of the invention will become apparent upon making reference to the specification, claims, and drawings to follow.

BRIEF DESCRIPTION OF THE DRAWINGS

FIG. 3 is an elevation view of the ostomy garment taken from the inside of the garment and substantially in the plane of the line 3—3 of FIG. 1;

FIG. 4 is a cross-sectional view of the ostomy garment substantially in the plane of the line 4—4 of FIG. 1;

FIG. 5 is a perspective view of another prior art ostomy garment as worn by a male user of an ostomy appliance;

FIG. 6 is a perspective view of another prior art ostomy garment as worn be a male user of an ostomy appliance;

FIG. 7 is a cross-sectional view of the ostomy garment substantially in the plane of the line 7—7 of FIG. 6;

FIG. 8 is a front elevation of the improved ostomy garment of the invention showing pocket panels in a separated condition;

FIG. 9 shows the garment of FIG. 8 wherein the corners of the pocket panels are being drawn towards each other;

FIG. 10 shows the securing of the pocket panels of FIGS. 8 and 9 together; and

FIG. 11 shows the final phase of adjustment of the garment shown in FIGS. 8, 9 and 10 wherein the outer garment is drawn over the ostomy device.

FIG. 12 shows an open-back version of the garment shown in FIG. 5.

DETAILED DESCRIPTION OF THE PREFERRED EMBODIMENT

Figure 1:
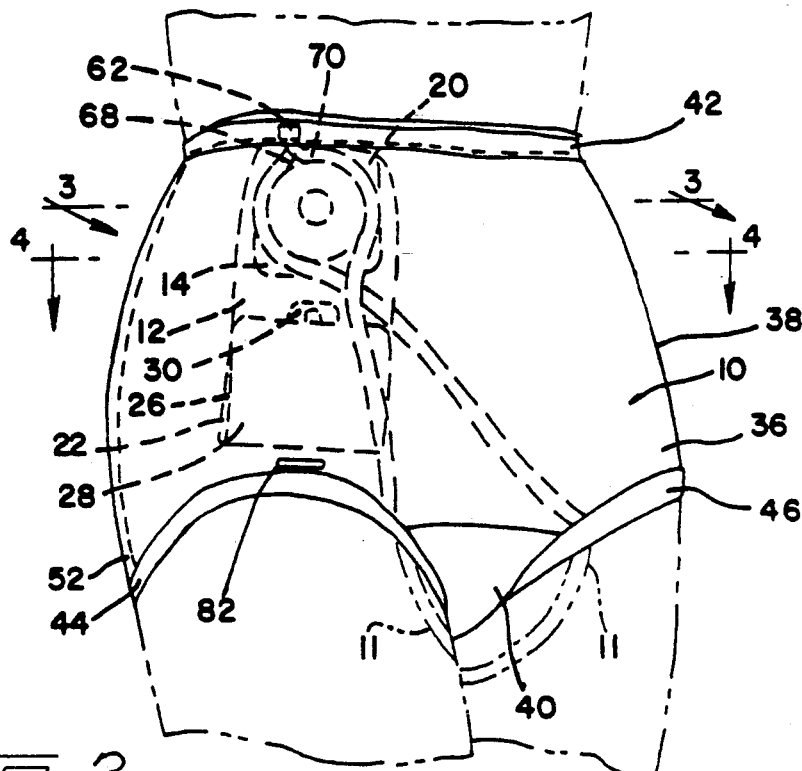
FIG. 1 is a perspective view of a prior art ostomy garment as worn by a female user of an ostomy appliance.

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to embodiment illustrated.

Figure 2:
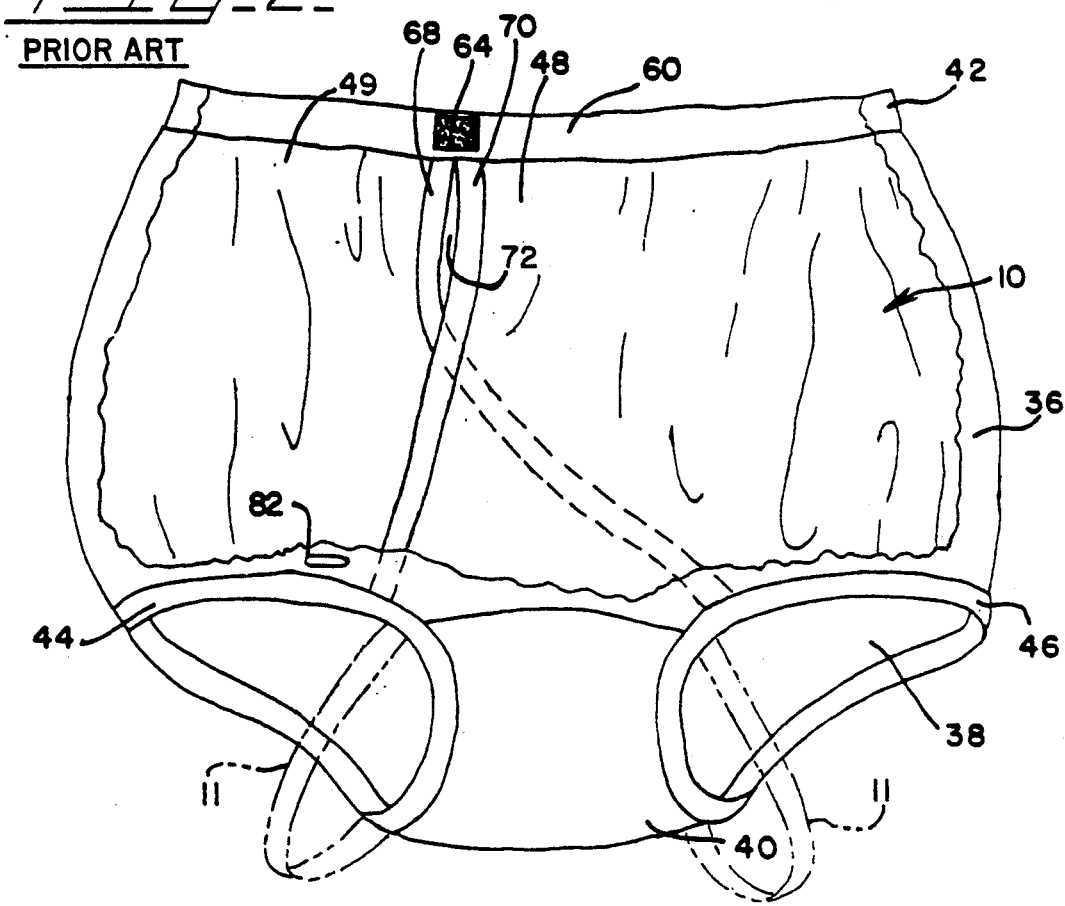
FIG. 2 is a front elevation view of the ostomy garment shown in FIG. 1, partly broken away, omitting the ostomy appliance.

Referring to the drawings and in particular to FIGS. 1–4, there is shown a prior art ostomy garment worn by a female user of a one or two piece ostomy appliance 12 generally referenced by 10. The supplemental leg bands 11 shown in FIGS. 1, 2 and 3 are not part of the prior art garment. Their function will be discussed subsequently. The ostomy appliance 12 generally comprises a wafer or apron 14 having a disc 16 fused with a circular wafer flange 18, which outer circumference is covered with an adhesive skin barrier portion 20 and a pouch 22 having a circular pouch flange 24 and two side walls 26,28 fused together, leaving an opening 30 distally positioned from the wafer which can be closed off with closures, clamps or irrigation valves.

Opposed to pouch opening 30, facing the user's abdomen, pouch flange 24 surrounds an opening 32 in side wall 28. Secured on the abdomen of the user by adhesive barrier 20, disc opening 34 receives the user's stoma and allows wafer flange 18 to extend away from the user's abdomen. Having compatible interlocking features, wafer flange 18 connects with the corresponding pouch flange 24. While a two piece ostomy appliance is referenced by the drawings, the garment can accommodate one or two piece appliances or "closed" appliances which do not provide for the distal opening 30 as referred herein.

Generally, ostomy garment 10 has front and back panels 36,38, a crotch panel 40 and a waist band 42 stitched together to construct a typical panty or undergarment. As shown in FIGS. 1 and 5, the prior art ostomy garment has leg bands 44,46 which can either hug the wearer's legs or flare as shown in FIG. 6. As can be readily visualized, the crotch panel 40 of the female garment can be provided with a slit to permit a female user to be sexually active without disturbance to the appliance 12. Also, releasable fasteners are preferably used to secure the crotch panel 40 to the front and back panels 36,35. Either configuration facilitates urination or airing.

With particular reference to FIGS. 2 and 3, a retaining pocket comprising a pair of pocket panels 48,49 are interposed between front panel 36 of garment 10 and abdomen of the user. Pocket panels 48,49 are disposed in a crisscross arrangement 50 over the abdomen of the user with side seams 52,54 of the garment 10 joining the outer sides of pocket panels 48,49 with front panel 36 of garment 10. The crisscross arrangement defines an opening through which the appliance flanges 18,24 extend, and will be described hereinafter.

The lower edges 56,57 of pocket panels 48,49 are stitched to the leg bands 44,46, respectively, and crotch panel 40 of the garment 10, as shown in FIG. 3. The waist band 60 of retaining pocket 48 is stitched to garment waist band 42 at the corresponding seams 52,54 of the garment. Corresponding members 62,64 of a fastener or closure device 66 are positioned on waist band members 42,60 proximate to the attachment of finished edges 68,70 of the crisscross arrangement 50 to the waist band 60.

The crisscross arrangement 50 of pocket panels 48,49 are created by finished edges 68,70 which are positioned off-center relative to front panel 36 of the garment 10. In this off-center position, finished edges 68,70 are stitched adjacent to one another with pocket waist band 60. Preferably, finished edges 68,70 are in juxtaposed abutting relation to each other, but could be slightly spaced, if desired, when stitched to pocket waist band 60. The finished edges 68,70 extend to the lower edges 56,57 of pocket panels 48,49 with edge 68 being stitched with leg band 46 and, similarly, edge 70 with leg band 44. The finished edges 68,70 overlap along their lower ends to define an adjustable, elongated, slanted slot 72.

When wearing ostomy garment 10 with appliance 12, finished edges 68,70 adjust and securely surround interlocked wafer flange 18 and pouch flange 24, allowing pouch 22 to pass through slot 72, to be retained by pocket panels 48,49. With edges 68,70 surrounding flanges 18 and 24, retaining pocket panels 48,49 are positioned between pouch 22 and the abdomen of the user, acting as a moisture barrier for the comfort of the user. While pocket panels 48,49 are preferably of a cotton or cotton blend fabric, other barrier materials may be used.

Convenient access to pouch 22 is provided by unfastening closure device 66 while the garment 10 is being worn by the user, to facilitate maintenance of the appliance 12. Worn in this manner, retaining pocket panels 48,49 also provide a barrier between adhesive barrier 20 and pouch 22. Further, the secure surrounding of flanges 10, 24 by the crisscross arrangement 50 and the containment of pouch 22 by retaining pocket panels 48,49 provide sufficient support for appliance 12 regardless of the position or activity of the user.

Referring to FIG. 5, a jockey style brief 10' can be adapted to the system described above. The brief 10' can be provided with an additional closure device 74 on front panel 36' to permit the triangle-shaped portion of front panel 36' to be folded toward the user's body and crotch panel 40', thereby allowing access to the penis without disturbance to the appliance 12'.

An additional embodiment adapted to a boxer style brief 10'', is shown in FIG. 6. Shown as worn by a male user of one or two piece ostomy appliance 12, the construction of which has been previously described. Boxer style garment 10'' is of a typical construction having front and back panels 36'',38'', a crotch panel 40'', a waist band 42'' and leg bands 44'',46''.

Retaining pocket panels 48'',49'' having a similar crisscross arrangement 50'' are interposed between front panel 36'' and the user's abdomen. Rather than stitch the lower edge 56'' of retaining pocket 48'' to leg bands 44'',46'' and crotch panel 40'', thereby restricting the activities a male wearer, pocket panel lower edges 56'',57'' are stitched to lower edge 75 of an insert panel 58 interposed between front panel 36'' and retaining pocket panels 48'',49''. Insert panel 58 has side edges 76,78 stitched with seams 52'' and 54'', respectively and an upper edge stitched with waist band 42'' of garment 10''. Corresponding members 62'',64'' of a fastener or closure device 66'' are positioned on edge 80 and pocket waist band 60'' proximate to the off-center attachment of finished edges 68'' and 70'' of crisscross arrangement 50'' to waist band 60''.

When wearing ostomy garment 10'' with appliance 12'', the crisscross arrangement 50'' of retaining pocket panels 48'',49'' similarly provides for the secure surrounding of flanges 18'' and 24'' while pouch 22'' passes through slot 72''. Once through slot 72'', pouch 24'' is retained between pocket panels 48'',49'' and insert panel 58 without restricting the position or activity of the male user.

Further, ostomy garments 10,10',10'' can be provided with a slit 82,82',82'' in front panel 36,36',36'' respectively to permit passage of a catheter.

In addition, these prior art ostomy garments 10,10',10'' can be worn in conjunction with an ostomy appliance provided with or used with a belt device which encircles the user's trunk. When worn with such a belt device, neither the belt nor the prior art garments described hereinabove require any adaptation.

Referring now in particular to FIGS. 8 and 11, an improved version of the above described prior art garments is shown. The illustrative example shown in FIGS. 8 and 11 is particularized to the modification of the garment shown in FIGS. 1-4, wherever appropriate, identical figure element designation numbers are employed. As best seen in FIG. 8, the pocket panels 48,49 are no longer permanently secured together at the top. Panel 49 has affixed to the outer edge 102 thereof an outwardly facing strip of self-adhering cloth of the type marketed under the trade name Velcro. Similarly, extending from the upper edge 100 of panel 48 there is provided an extension tab 106 having a similar material on the interior face thereof.

The garment is initially positioned on the user as shown in FIG. 8 with the front garment panel 36 pulled down. As shown in FIG. 9, the garment front panel 36 is moved in behind the lower portion of the ostomy appliance 12, and the panels 48,49 are similarly so emplaced. The upper panel region 104 and the extension tape 106 are drawn together in an overlapping relationship as shown. Pressing the two tapes 104,106 together secures the panels 48,49 in place with edges 68,70 securely surrounding the ostomy device flange 24. Finally, as shown in FIG. 11, the lower portion of the ostomy device 12 is inserted behind the garment front panel 36, and the garment front panel may then be drawn up into final position.

As is clear from the drawings, engagement of the two tapes 104,106 may cause the positions of the top of the edges 68,70 to be either widely separated or overlapping, thereby providing the user with a measure of control of the tension in the garment and the degree of surrounding of the rear portion of the ostomy device 12. Identical principles may be applied to the mens' garments shown in FIGS. 5 and 6.

FIG. 12 shows an open-back version 10''' of the garment shown in FIGS. 8-11. Here the rear panel 38 (see FIGS. 2 and 4) is removed completely. The lower portion of the front panel is secured to the legs of the user by bands 11. This provides for a cooler and less confining garment for bedtime wear. A crotch panel 40 is attached to the front panel 36 and to the leg bands preferably by snap fasteners 10 to permit removal. Additional fasteners (not shown) fasten the rear of the crotch panel 40 to rear portions of the leg bands 11. Such leg bands 11 may similarly be affixed to the garments shown in FIGS. 1-4, and 8-11 to provide additional security of retention.

While the invention has been described with reference to a preferred embodiment, it will be understood by those skilled in the art that various changes may be made and equivalents may be substituted for elements thereof without departing from the broader aspects of the invention. Also, it is intended that broad claims not specifying details of a particular embodiment disclosed herein as the best mode contemplated for carrying out the invention should not be limited to such details.

I claim:

1. An open-back undergarment for use in conjunction with an ostomy appliance having upper and lower pouch portions and a flange member mounted to said upper pouch portion comprising:
    a front panel forming the outer portion of said garment;
    a waistband connected to an upper edge of said front panel;
    a pair of leg bands having only portions thereof connected to lower edges of said front panel; and
    retaining pocket means confronting the rear surface of said front panel for receiving an ostomy appliance and connected to said front panel and said leg bands, said retaining pocket means including first and second pocket panels each attached at the lower edges thereof to a lower portion of said front panel and having lower side edge portions configured for criss-cross overlapping confrontation for confining the lower portion of said appliance above the region of overlap and upper side edge portions configured to be engagingly drawn around opposite portions of said flange so that said edge portions form a barrier between the appliance pouch and the user, said side edge portions being movable with respect to each other over at least a portion thereof below said overlap so that the upper terminus of said overlap defines the lower end of an adjustable slot for accommodating a range of positions of said flange.

2. The undergarment of claim 1 including first releasable fastening means for securing said upper edge portions together above said flange over a range of fastening positions.

3. The undergarment of claim 1 wherein said first releasable fastening means includes strips of mutually adherable fabric attached to said upper edge portions and configured for confronting overlapping engagement over said range of fastening positions.

4. The undergarment of claim 1 wherein said overlap region is located off-center with respect to the centerline of said front panel.

5. The undergarment of claim 1 including a crotch panel and second releasable fastening means for attaching said crotch panel to the central lower portion of said front panel and to portions of said leg bands.

6. The undergarment of claim 5 wherein said second fastening means includes snap-together fastener means.

7. The undergarment of claim 1 including third releasable fastening means for securing portions of the upper edges of said first and second panels to said waistband.

8. The undergarment of claim 1 wherein said pocket panels are made of moisture-absorbing material.

9. An undergarment for use in conjunction with an ostomy appliance having upper and lower pouch portions and a flange member mounted to said upper pouch portion comprising:
    front, back and crotch garment panels interconnected together to form the outer portion of said garment and configured to form a waistband at the top thereof;
    retaining pocket means interposed between said front and back garment panels for receiving an ostomy appliance and connected to one of said front and said back garment panels, said retaining pocket means including first and second pocket panels each attached at the lower edges thereof to a lower portion of said front panel and having lower side edge portions configured for criss-cross overlapping confrontation for confining the lower portion of said appliance above the region of overlap and upper side edge portions configured to be engagingly drawn around opposite portions of said flange so that said edge portions form a barrier between the appliance pouch and the user, said side edge portions being movable with respect to each other over at least a portion thereof below said overlap so that the upper terminus of said overlap defines the lower end of an adjustable slot for accommodating a range of positions of said flange, each of said first and second pocket panels being secured at lower edges thereof to a lower portion of said front panel; and first releasable fastening means for securing said upper edge portions together above said flange over a range of fastening positions.

10. The undergarment of claim 9 including a pair of leg band means each attached only along portions thereof to portions of the lower edges of said front and back panels for securing said undergarment to the legs of the user.

11. The undergarment of claim 9 including second releasable fastening means for removably affixing said crotch panel to the lower edges of said front and back panels.

12. The undergarment of claim 9 including third releasable fastening means for securing said upper edge portions of said pocket panels to said waistband.

13. The undergarment of claim 9 wherein said overlap region is located off-center with respect to the centerline of said front panel.

14. The undergarment of claim 9 wherein said first releasable fastening means includes strips of mutually adherable fabric attached to said upper edge portions and configured for confronting overlapping engagement over said range of fastening positions.

15. The undergarment of claim 9 wherein said pocket panels are made of moisture-absorbing material.

16. An undergarment for use in conjunction with an ostomy appliance having upper and lower pouch portions and a flange member mounted to said upper pouch portion comprising:

front, back and crotch garment panels interconnected together to form the outer portion of said garment and configured to form a waistband at the top thereof;

retaining pocket means interposed between said front and back garment panels for receiving an ostomy appliance and including first and second pocket panels having lower side edge portions configured for criss-cross overlapping confrontation for confining the lower portion of said appliance above the region of overlap and upper side edge portions configured to be engagingly drawn around opposite portions of said flange so that said edge portions form a barrier between the appliance pouch and the user, said side edge portions being movable with respect to each other over at least a portion thereof below said overlap so that the upper terminus of said overlap defines the lower end of an adjustable slot for accommodating a range of positions of said flange, and an insert panel interposed between said back garment panel and said pocket panels and affixed at the lower edge thereof to the lower edges of said pocket panels; and first releasable fastening means for securing said upper side edge portions together above said flange over a range of fastening positions.

17. The undergarment of claim 16 including second releasable fastening means for securing said upper edge portions of said pocket panels to said waistband.

18. The undergarment of claim 16 wherein said overlap region is located off-center with respect to the centerline of said front panel.

19. The undergarment of claim 16 wherein said first releasable fastening means includes strips of mutually adherable fabric attached to said upper edge portions and configured for confronting overlapping engagement over said range of fastening positions.

20. The undergarment of claim 16 wherein said pocket panels and said insert panel are made of moisture-absorbing material.

* * * * *